Nov. 10, 1953 H. C. PETERSON Plant Pat. 1,228
PEACH TREE
Filed Oct. 7, 1952
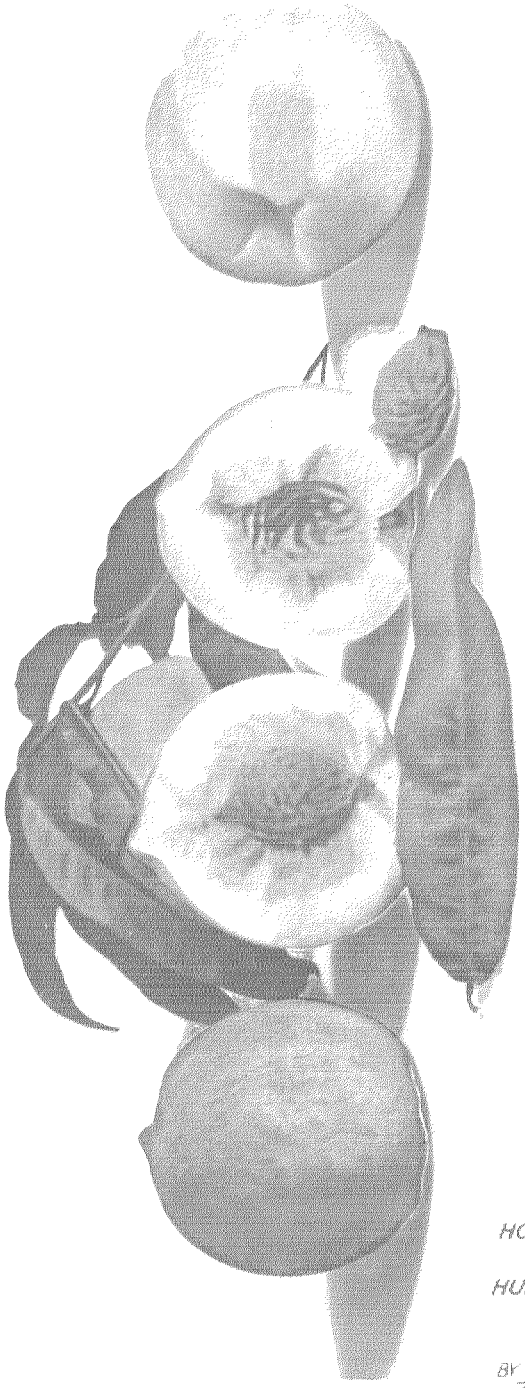
HOWARD C. PETERSON
INVENTOR
HUEBNER, BEEHLER,
WORREL & HERZIG
ATTORNEYS
BY Richard M. Worrel Patented Nov. 10, 1953

Plant Pat. 1,228

UNITED STATES PATENT OFFICE 1,228

PEACH TREE

Howard C. Peterson, Reedley, Calif.

Application October 7, 1952, Serial No. 313,621

1 Claim. (Cl. 47—62)

The present discovery relates to a new variety of peach tree which originated as a bud sport of the well-known "Stark Early Elberta," unpatented, peach tree and was discovered by me in my orchard.

Although an offspring of the "Stark Early Elberta," the instant peach tree more closely resembles the popular "Kim Elberta" (unpatented) and the fruit thereof the "Rio Oso Gem" (Plant Patent No. 84). Its most striking visual characteristic is its brilliant fruit splotched with scarlet red which at maturity clearly distinguishes the tree from its parent, from the "Kim Elberta," and from the "Rio Oso Gem." The "Christofferson" peach (Plant Patent No. 970) is believed most nearly to approach the instant peach in skin coloration but the red thereof is not quite as brilliant although more extensive in per cent of skin area covered. The "Christofferson" peach is not grown extensively in California, however, and the color comparisons therewith are subject to some error. My new peach ripens about ten days later than the "Vetter" peach (Plant Patent No. 966), a week earlier than the "Kim Elberta," twenty to thirty days earlier than the "Christofferson" peach, and approximately six weeks before the "Rio Oso Gem." It characteristically has a smaller pit and proportionately thicker flesh than either the "Kim Elberta" or the "Rio Oso Gem." It colors and sizes earlier in its process of maturation than most peaches and thus may be picked correspondingly earlier for shipment, a valuable attribute in commercial peach production.

It will be recognized that the present peach fulfills a commercially desirable demand for a peach having yellow flesh which ripens between the "Vetter" peach and the "Kim Elberta." The brilliant scarlet red streaking of the flesh of the subject peach, particularly near the pit well, is vividly contrasted with the yellow pit well of the "Vetter" peach and is more brilliant than the pit well of the "Kim Elberta."

This new peach is aptly described as a slightly tight freestone. When the fruit is fully ripe, its fruit recedes from the pit leaving only thin filaments or strands adhering to the pit. The peach is more clearly freestone than the semi-freestone "Christofferson" peach and slightly less free than the "Kim Elberta."

Considering other general characteristics of the present peach, it is worthy of note that its blooming period is somewhat shorter and a few days later than the usual blooming period of the "Kim Elberta." Its blossoms are slightly smaller and do not open quite as fully as those of the "Kim Elberta." When grown adjacent to "Kim Elberta" trees, the present variety is not only distinguished therefrom by the greater brilliance of its fruit but by a slightly lighter colored foliage and usually by not quite as numerous leaves.

Asexual reproduction of this new variety on my farm near Reedley, county of Fresno, and State of California, show the described characteristics to be consistent and well established.

The reproduction has been accomplished by budding and by grafting. The new variety has been budded successfully into such trees as the Kim Elberta peach, an unnamed experimental peach, the Eldorado plum, the Emily plum, the Lovel peach, all believed to be unpatented, and other peach trees. It has been successfully grafted into both early and late Sunbeam peach trees, believed to be unpatented, and others.

In the accompanying drawing are shown characteristic fruit and leaves of my new variety peach. In order to display the distinctive coloring of the flesh of the subject peach, two peach halves are shown.

The following detailed description generally follows the outline suggested by U. P. Hedrick in his book entitled Systematic Pomology published in 1925 and the color terminology is employed as accurately in accordance with Ridgway's Color Standards and Color Nomenclature published in 1912 as practical comparisons permit.

*Tree*

General characteristics: Medium size, vigorous, upright to spreading, somewhat open, generally round topped, hardy, productive, and regular bearer.

Trunk: Medium stocky, and medium smooth.

Branches: Reasonably stocky, smooth, varying in color from russet, Plate XV–13′–*k*, to garnet brown, Plate I–3–*k*, to grass green, Plate VI–33–*k*.

Lenticels: Medium in size and number.

Leaves: Average length when mature approximately 6½ inches. Average width mature about 1⅜ inches. Large, acuminate, lanceolate, acutely pointed smooth surfaced, few glands, edges very minutely serrated and slightly wavy. Surfaces approximately forest green in color, Plate XVII–29′–*m*, and veins approximately courge green, Plate XVII25′–*i*. Petiole medium length, long grooved, usually with none to four glands. Blend from garnet brown or morocco red, Plate I–5–*k*, to grass green during rapid growth.

*Blossoms*

Somewhat smaller than average being approximately two-thirds as long as those of the "Kim Elberta," slightly darker pink than "Kim Elberta," and not as widely opened. Blooms for a shorter period of time than "Kim Elberta" and slightly later although overlapping. Average blooming period in San Joaquin Valley of California about March 2nd to March 8th.

*Fruit*

The fruit is of high quality, attractive appearance, and ships well.

Ripening period: In San Joaquin Valley approximately June 20th to June 25th.

Size: Large, average longitudinal diameter 3½ inches, average transverse diameter in suture plane 3¼ inches, average transverse diameter normal to suture plane 3⅛ inches.

Form: Uniform, symmetrical, globose, very slightly compressed, and slightly pointed.

*Suture.*—Occasionally deep at stem and usually extending approximately half-way toward the pistil point.

*Stem end.*—Retuse with deep depression.

*Pit well.*—When sliced in suture plane approximately 1½ inches long, 1¼ inches wide and ¾ inches deep. Scarlet red, Plate I–3–, in depressions and capucine yellow, Plate III–13–*d* on ridges.

*Apex.*—Varied from slightly retuse to small sharply pointed pistil point.

Flesh: Relatively firm.

*Color.*—Light orange yellow, Plate III–17–*d* normally with extensive brilliant scarlet red streaking, Plate I–3–, from the pit well a considerable distance into the flesh. The extent of scarlet red streaking appears to vary somewhat according to the climatic environment under which the fruit is matured, being somewhat less extensive when matured at lower temperatures.

Skin: Medium thickness, tenacious to flesh except where over ripe or bruised, no noticeable tendencies to crack, and pubescent. Pubescence, short, thin but present in sufficient quantity to roll when rubbed.

*Background.*—Skin coloring varies from light orange yellow, Plate III–17–*d*, to capucine yellow, Plate III–13–*d*, to cinnamon orange, Plate II–2–*d*.

*Skin color splotches.*—Mottled with scarlet red, Plate I–3–, to nopal red on sunny side particularly and extensively throughout when mature.

*Amygadalin.*—Juice moderate.

*Fibres.*—Light orange yellow, fine, and tender.

*Flavor.*—Mildly acid and sweet.

*Juice.*—Moderate.

*Aroma.*—Slight.

*Eating quality.*—Excellent.

*Ripens.*—Evenly.

Stone: Free but tight when not fully ripe, parts from flesh smoothly but frequently retains thin filaments of flesh along ridges near base.

*Size.*—Medium, average length 1½ inches, average width 1 inch, average thickness ⅝ inch.

*Fibres.*—Few on grooved side.

*Form.*—Obovate, tip acuminate.

*Base.*—Long tapering.

*Hilum.*—Oval and shallow.

*Apex.*—Acuminate.

*Sides.*—Substantially symmetrical.

*Surface.*—Deeply grooved and pitted, grooves more pronounced on dorsal side, interrupted blades on ventral side.

*Color.*—Approximately fawn color, Plate XL–13'''–, with scarlet red streaks on ridges.

*Tendency to split.*—Slight but noticeable.

Use: Excellent for dessert, culinary uses, canning, freezing, and shipment.

Keeping quality: Excellent. Firm flesh resists deterioration and browning for protracted periods even when exposed to air.

The subject peach tree and its fruit may vary in minor particulars due to climatic, soil, and other environmental variations but has been described as observed under cultivation in the San Joaquin Valley of California.

Having thus described my discovery, I claim:

A new and distinct variety of peach tree, substantially as described and illustrated, bearing freestone fruit of generally light orange-yellow to salmon-orange color having splotches over extensive areas of scarlet red to nopal red and of the general shape of the Rio Oso Gem but more symmetrical and ripening about six weeks earlier, characterized by early coloring during maturation permitting picking for shipment in durable condition prior to full ripening; having flesh varied in color from light orange-yellow to capucine yellow prominently streaked with scarlet red when mature similarly to the Kim Elberta but more brilliantly and ripening about one week earlier than the Kim Elberta; and blossoming at approximately the same time as the Kim Elberta with blossoms about two-thirds as large and less widely opened.

HOWARD C. PETERSON.

No references cited.